(12) United States Patent
Pradhan et al.

(10) Patent No.: US 9,359,341 B2
(45) Date of Patent: Jun. 7, 2016

(54) ALDEHYDE DERIVATIVE OF SUBSTITUTE OXAZOLIDINONES

(71) Applicant: WANBURY LTD., Navi Mumbai, Maharashtra (IN)

(72) Inventors: Nitin Sharadchandra Pradhan, Maharastra (IN); Nilesh Sudhir Patil, Maharastra (IN); Rajesh Ramchandra Walavalkar, Maharastra (IN); Nilesh Subhas Kulkarni, Maharastra (IN); Sandip Babanrao Pawar, Maharastra (IN); Tarak Sambhaji Pawar, Maharastra (IN)

(73) Assignee: WANBURY LTD., Navi Mumbai, Maharashtra ( * ) Notice: Subject to any disclaimer, the term of this patent is extended or adjusted under 35 U.S.C. 154(b) by 0 days.

(21) Appl. No.: 14/436,018

(22) PCT Filed: Dec. 24, 2013

(86) PCT No.: PCT/IN2013/000801
§ 371 (c)(1),
(2) Date: Apr. 15, 2015

(87) PCT Pub. No.: WO2014/102822
PCT Pub. Date: Jul. 3, 2014

(65) Prior Publication Data
US 2015/0259333 A1    Sep. 17, 2015

(30) Foreign Application Priority Data
Dec. 26, 2012    (IN) .......................... 3359/MUM/2012

(51) Int. Cl.
*A61K 31/5377* (2006.01)
*C07D 413/14* (2006.01)
*C07D 413/10* (2006.01)

(52) U.S. Cl.
CPC .......... *C07D 413/14* (2013.01); *A61K 31/5377* (2013.01); *C07D 413/10* (2013.01)

(58) Field of Classification Search
CPC . C07D 413/10; C07D 413/14; A61K 31/5377
See application file for complete search history.

(56) References Cited

U.S. PATENT DOCUMENTS

| 7,157,456 | B2 | 1/2007 | Straub et al. | |
|---|---|---|---|---|
| 7,351,823 | B2 | 4/2008 | Berwe et al. | |
| 7,585,860 | B2 | 9/2009 | Straub et al. | |
| 7,592,339 | B2 | 9/2009 | Straub et al. | |
| 7,767,702 | B2 * | 8/2010 | Straub | A61K 31/421 514/376 |
| 7,932,278 | B2 | 4/2011 | Thomas et al. | |
| 8,101,601 | B2 | 1/2012 | Lerchen et al. | |
| 8,334,284 | B2 * | 12/2012 | Lerchen | C07D 413/14 514/230.8 |
| 8,362,015 | B2 * | 1/2013 | Lerchen | C07D 413/14 514/236.8 |
| 8,946,224 | B2 * | 2/2015 | Craighead | C07C 217/58 514/249 |
| 2003/0153610 | A1 | 8/2003 | Straub et al. | |
| 2010/0063278 | A1 | 3/2010 | Bracken et al. | |

FOREIGN PATENT DOCUMENTS

| WO | 0147919 A1 | 7/2001 |
|---|---|---|
| WO | 2004060887 A1 | 7/2004 |
| WO | 2007039132 A1 | 4/2007 |
| WO | 2009023233 A1 | 2/2009 |
| WO | 2010124385 A1 | 11/2010 |
| WO | 2011012321 A1 | 2/2011 |
| WO | 2011080341 A1 | 7/2011 |
| WO | 2011098501 A1 | 8/2011 |
| WO | 2012140061 A1 | 10/2012 |
| WO | 2012153155 A1 | 11/2012 |
| WO | 2012159992 A1 | 11/2012 |
| WO | 2014102820 A1 | 7/2014 |

OTHER PUBLICATIONS

Jianyong Yuan et al., A Novel Synthesis of the Oxazolidinone Antithrombotic Agent Rivaroxaban, Molecules, 2014, p. 14999-15004, vol. No. 19, Issue No. 9.
Susanne Roehrig et al., Discovery of the Novel Antithrombotic Agent 5-Chloro-N-({(5 S )-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor, Journal of Medicinal Chemistry, 2005, pp. 5900-5908, vol. No. 48, Issue No. 19.
James L. Kelley et al., 6-(Alkylamino)-9-Alkylpurines. A New Class of Potential Antipsychotic Agents, J. Med. Chem, 1997, p. 3207-3216, vol. No. 40.
United States Patent and Trademark Office (ISR/US), "International Search Report for PCT/IN2013/000801", US, Aug. 12, 2015.

* cited by examiner

*Primary Examiner* — Rebecca Anderson
(74) *Attorney, Agent, or Firm* — Tim Tingkang Xia, Esq.; Locke Lord LLP

(57) ABSTRACT

The present invention relates to the prodrug of 5-chloro-N-({(5S)-2-oxo-3-[4-(3-oxo-morpholin-4-yl)phenyl]-1,3-oxazolidin-5-yl}methyl)thiophene-2-carboxamide, rivaroxaban per se; processes for their preparation, and the application in treatment and/or prophylaxis of diseases, especially of thromboembolic disorders. The prodrug of a compound of formula (B) is chemically designated as 5-chloro-N-formyl-N-({(5S)-2-oxo-3-[4-(3-oxomorpholin-4-yl)phenyl]-1,3-oxazolidin-5-yl}methyl)thiophene-2-carboxamide.

Formula (B)

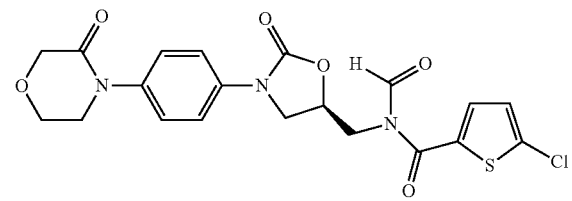

9 Claims, No Drawings

ALDEHYDE DERIVATIVE OF SUBSTITUTE OXAZOLIDINONES

FIELD OF THE INVENTION

The present invention mainly relates to the aldehyde derivative of Substituted oxazolidinones and more particularly to a prodrug of 5-chloro-N-({(5S)-2-oxo-3-[4-(3-oxo-morpholin-4-yl)phenyl]-1,3-oxazolidin-5-yl}methyl) thiophene-2-carboxamide, and the process for preparation of prodrug. The prodrug of formula (B); is chemically designated as 5-chloro-N-formyl-N-({(5S)-2-oxo-3-[4-(3-oxo-morpholin-4-yl)phenyl]-1,3-oxazolidin-5 yl}methyl) thiophene-2-carboxamide, or pharmaceutically accepted salt or solvate form or hydrate form. Further this invention relates to the use of prodrug in treatment of prophylaxis of diseases, pulmonary embolism, and deep venous thrombosis more particularly to thromboembolic disorder.

Formula (B)

BACKGROUND OF THE INVENTION

A large number of medicaments are administered as prodrugs which exhibits an improved bioavailability by comparison with the underlying active ingredient, for example, by improving the physicochemical profile, specifically the solubility, the active or passive absorption properties or the tissue-specific distribution. In order to achieve an optimal profile of effects it is necessary for the design of the prodrug residue as well as the desired mechanism of liberation to conform very accurately to the individual active ingredient, the indication, the site of action and the administration route The importance of the prodrug is more, when the main moiety raises concerns of solubility, stability and oral bioavailability.

Rivaroxaban is an orally active direct factor Xa (FXa) inhibitor drug, used for the prevention and treatment of various thromboembolic diseases, in particular pulmonary embolism, deep venous thrombosis, myocardial infarction, angina pectoris, reocclusion and restenosis after angioplasty or aortocoronary bypass, cerebral stroke, transitory ischemic attacks, and peripheral arterial occlusive diseases.

Rivaroxaban i.e. 5-chloro-N-({(5S)-2-oxo-3-[4-(3-oxo-morpholin-4-yl)phenyl]-1,3-oxazolidin-5-yl}methyl) thiophene-2-carboxamide, has a CAS number of 366789-02-8, a molecular formula of $C_{19}H_{18}ClN_3O_5S$, and the following structure:

Formula (I)

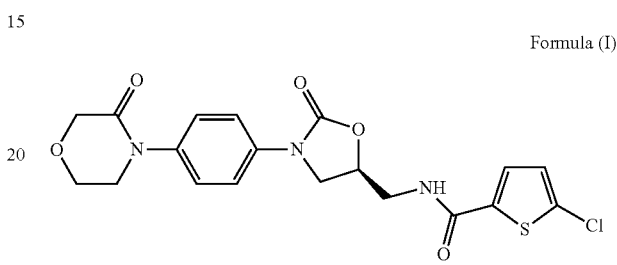

Rivaroxaban, though effective for prevention and treatment of various thromboembolic diseases, often raises issue of dosage and relative bio availability.

WO 01/47919, application disclosed the Rivaroxaban with applications for prevention and treatment of various thromboembolic diseases. Further this patent describes a method for preparation of Rivaroxaban of formula (I), wherein 4-(4-aminophenyl)morpholin-3-one is reacted with 2-[(2S)-oxiran-2-ylmethyl]-1H-isoindole-1,3(2H)-dione, in presence of solvent to obtain 2-[(2R)-2-hydroxy-3-{[4-(3-oxomorpholin-4-yl)phenyl]amino}propyl]-1H-isoindole-1,3(2H)-dione which is further converted to 2-({(5S)-2-oxo-3-[4-(3-oxo-morpholin-4-yl)phenyl]-1,3-oxazolidin-5-yl}methyl)-1H-isoindole-1,3(2H)-dione by phosgene equivalent. Departing of the pthalamide group affords 4-{4-[(5S)-5-(aminomethyl)-2-oxo-1,3-oxazolidin-3-yl]phenyl}morpholin-3-one, which is finally coupled with 5-chlorothiophene-2-carbonyl chloride to give 5-chloro-N-({(5S)-2-oxo-3-[4-(3-oxomorpholin-4-yl)phenyl]-1,3-oxazolidin-5-yl}methyl)thiophene-2-carboxamide i.e. Rivaroxaban of formula (I) as shown in scheme-1;

Scheme-I

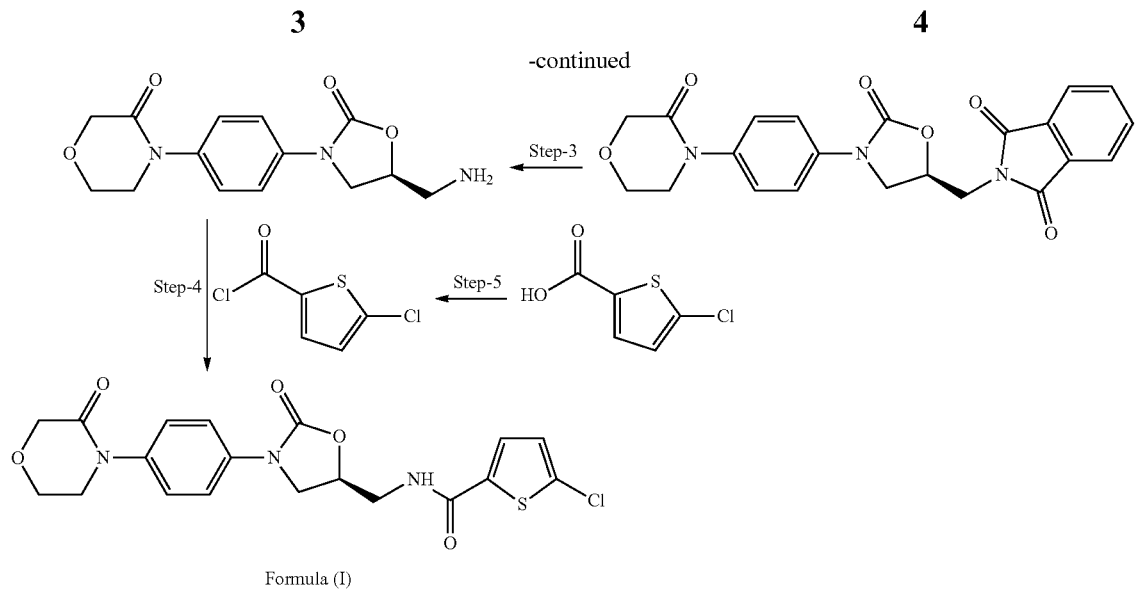

Formula (I)

The disclosed process, involves lengthy reaction periods, excess mole ratios of reactants and reagents, use of unsafe solvents such as methanol and methylene dichloride. Moreover title compound is isolated by column chromatography which is not feasible on commercial scale.

U.S. Pat. No. 7,932,278 B2, discloses the preparation of the compound Rivaroxaban by the synthesis scheme below:

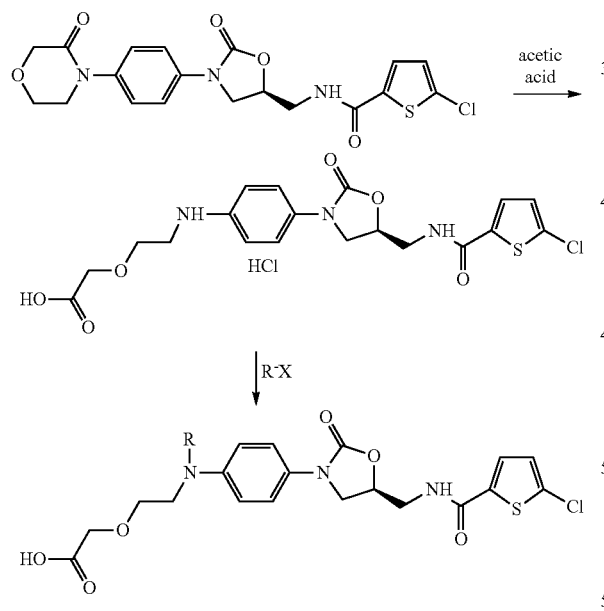

The compounds according to the invention are suitable for use as medicaments for the treatment and/or prophylaxis of diseases in humans and animals.

WO 2009/023233 discloses the compounds that are substituted oxazolidinones derivatives and pharmaceutically acceptable salts thereof. More specifically, this invention relates to novel oxazolidinones compounds that are derivatives of rivaroxaban. The invention also provides pyrogen-free compositions comprising one or more compounds of the invention and a carrier, and the use of the disclosed compounds and compositions in methods of treating diseases and condition that are beneficially treated by administering a selective inhibitor of factor Xa, such as rivaroxaban.

The present invention relates to a prodrug of Rivaroxaban. The compounds according to our instant invention are selective inhibitors of blood coagulation factor Xa which act in particular as anticoagulants, with favorable physicochemical properties, advantageous in therapeutic application such as treatment of thromboembolic disorders; inhibitor of factor Xa, and/or thromboembolic complications.

SUMMARY

In its main aspect, the present invention discloses a compound of formula (B), chemically designated as 5-chloro-N-formyl-N-({(5S)-2-oxo-3-[4-(3-oxomorpholin-4-yl)phenyl]-1,3-oxazolidin-5-yl}methyl)thiophene-2-carboxamide.

In another aspect, of the present invention discloses the use of the compounds of formula (B), for treatment and/or prophylaxis of disorders, such as thromboembolic disorders; inhibitor of factor Xa, and/or thromboembolic complications. The "thromboembolic disorders" include in the context of the present invention disorders such as myocardial infarction with ST segment elevation (STEMI) and without ST segment elevation (non-STEMI), stable angina pectoris, unstable angina pectoris, reocclusions and resteneses following coronary interventions such as angioplasty or aortocoronary bypass, peripheral arterial occlusive diseases, pulmonary embolisms, deep venous thromboses and renal vein thromboses, transient ischaemic attacks, and thrombotic and thromboembolic stroke.

In yet another aspect, the present invention discloses a use of the compound formula (B) for prevention and treatment of cardiogenic thromboembolisms, such as, for example, cerebral ischaemias, stroke and systemic thromoboembolisms and ischaemias, in patients with acute, intermittent or persistent cardiac arrhythmias such as, for example, atrial fibrillation, and those undergoing cardioversion, also in patients with heart valve diseases or with artificial heart valves. The compound according to the invention is additionally suitable for the treatment of disseminated intravascular coagulation (DIC).

Another aspect of the present invention is to provide the process for the preparation of the compound formula (B) which is substantially free from impurities.

Yet another aspect of the present invention is to provide compound formula (B) in crystalline or amorphous form.

Yet another aspect, the present invention discloses a compound formula (B) in a pharmaceutically accepted salt or hydrate form or solvate form of compound formula (B).

DETAILED DESCRIPTION OF THE INVENTION

In its main embodiment, the present invention comprises the compound formula (B), chemically designated as 5-chloro-N-formyl-N-({(5S)-2-oxo-3-[4-(3-oxomorpholin-4-yl)phenyl]-1,3-oxazolidin-5-yl}methyl)thiophene-2-carboxamide, having the structure:

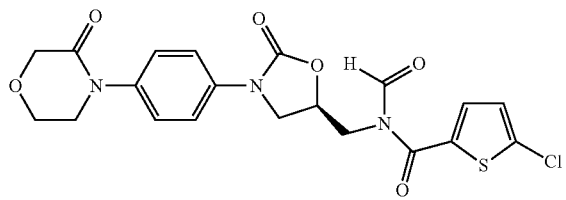

Formula (B)

Or its pharmaceutically accepted salt or solvate form or hydrate form, which acts as a prodrug of for compound formula (I) chemically designated as 5-chloro-N-({(5S)-2-oxo-3-[4-(3-oxomorpholin-4-yl)phenyl]-1,3-oxazolidin-5-yl}methyl)thiophene-2-carboxamide, having the structure:

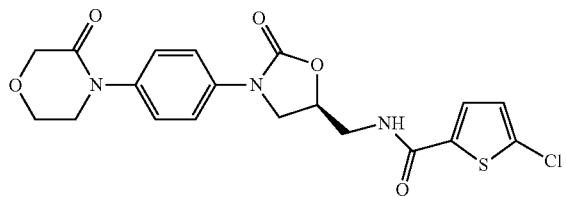

Formula (I)

The word prodrug includes the compound which may be pharmacologically active or inactive, but on ingestion is enzymatically or hydrolytically converted by the body in to the active compound. The present invention focuses on these concerns The compound of formula (B), as disclosed in vitro and in vivo animal studies has shown superior solubility and stability as is explicitly reflected in the examples, and hence encourage clinical trials.

The present compound formula (B), exists in stereoisomeric forms (enantiomers, diastereomers). Accordingly, the invention comprises the enantiomers or diastereomers and their respective mixtures. From such mixtures of enantiomers and/or diastereomers, it is possible to isolate the stereoisomerically uniform components in a known manner. If the compounds according to the invention can be present in tautomeric forms, the present invention comprises all tautomeric forms.

The present invention carried out the detailed study on the solubility, stability and liberation behavior of the invented compound (compound formula B). Further INVITRO and INVIVO studies for compound formula (B) are carried out in order to established the selective activity such as In Vitro Liver Microsomal Stability Assay, In Vitro Stability in Rat, Mouse and Human Plasma, CYP Inhibition Assay, Plasma Protein Binding Intravenous and Oral Pharmacokinetics in Wistar Rats, Suspension for Intravenous Administration and Solution for Oral Administration, anticoagulant activity and Antithrombotic activity, wherein theses study are well exemplified or illustrated with best mode in examples section/example (B).

In an important embodiment, the present invention provides for a process for the preparation of compound formula (B) comprising of:

a) reacting, 4-(4-aminophenyl)morpholine-3-one of formula (II) with 2-[(2S)-oxiran-2-ylmethyl]-1H-isoindole-1,3(2H)-dione of formula (III) in a suitable solvent to obtain 2-[(2R)-2-hydroxy-3-{[4-(3-oxomorpholin-4-yl)phenyl]amino}propyl]-1H-isoindole-1,3(2H)-dione of formula (IV);

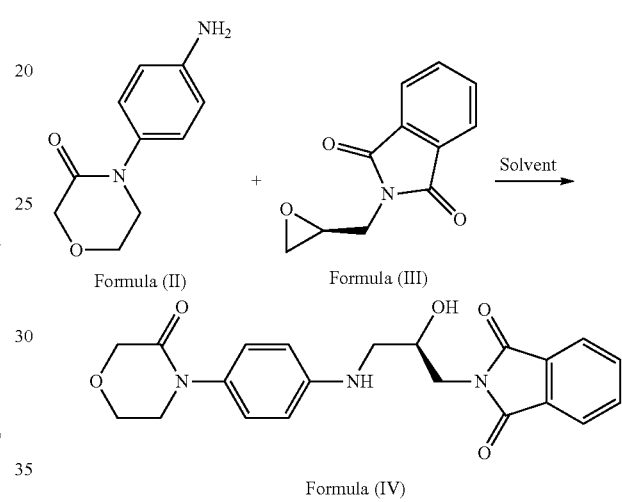

b) preparing compound of formula (VI) by reacting compound of formula (IV) with di-1H-imidazol-1-ylmethanone of formula (V);

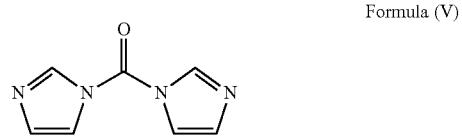 [SMILES: O=C(n1ccnc1)n1ccnc1]

Formula (V)

In the alternative, in a suitable solvent compound of formula IV is converted to a compound of formula VI in the presence of a base.

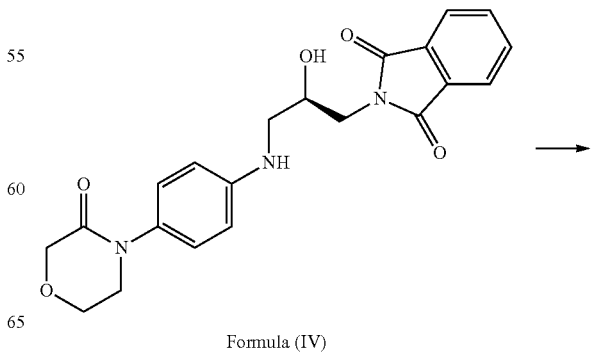

Formula (IV)

-continued

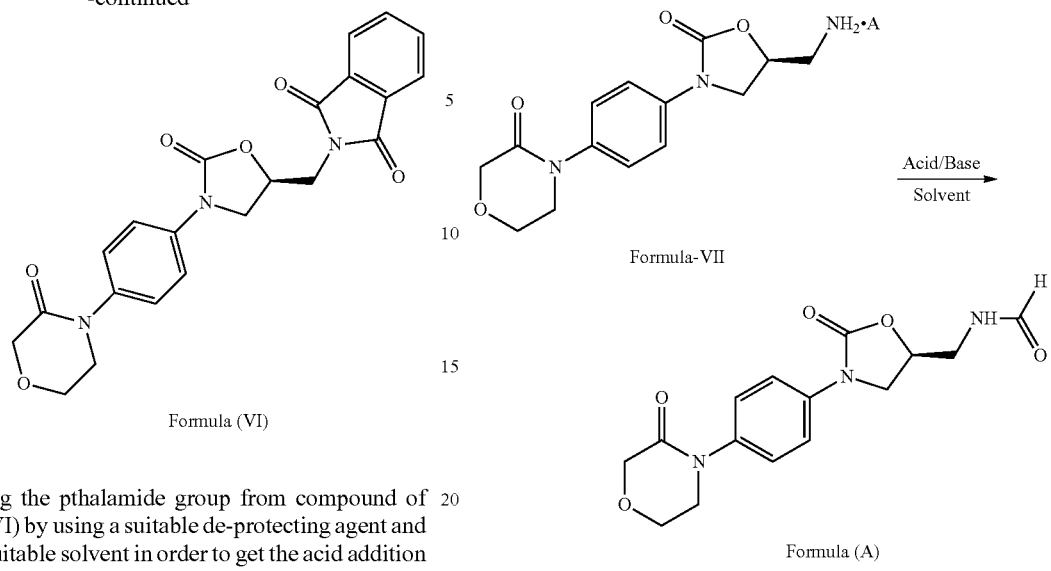

c) eliminating the pthalamide group from compound of formula (VI) by using a suitable de-protecting agent and acid in a suitable solvent in order to get the acid addition salt of 4-{4-[(5S)-5-(aminomethyl)-2-oxo-1,3-oxazolidin-3-yl]phenyl}morpholin-3-one formula (VII).

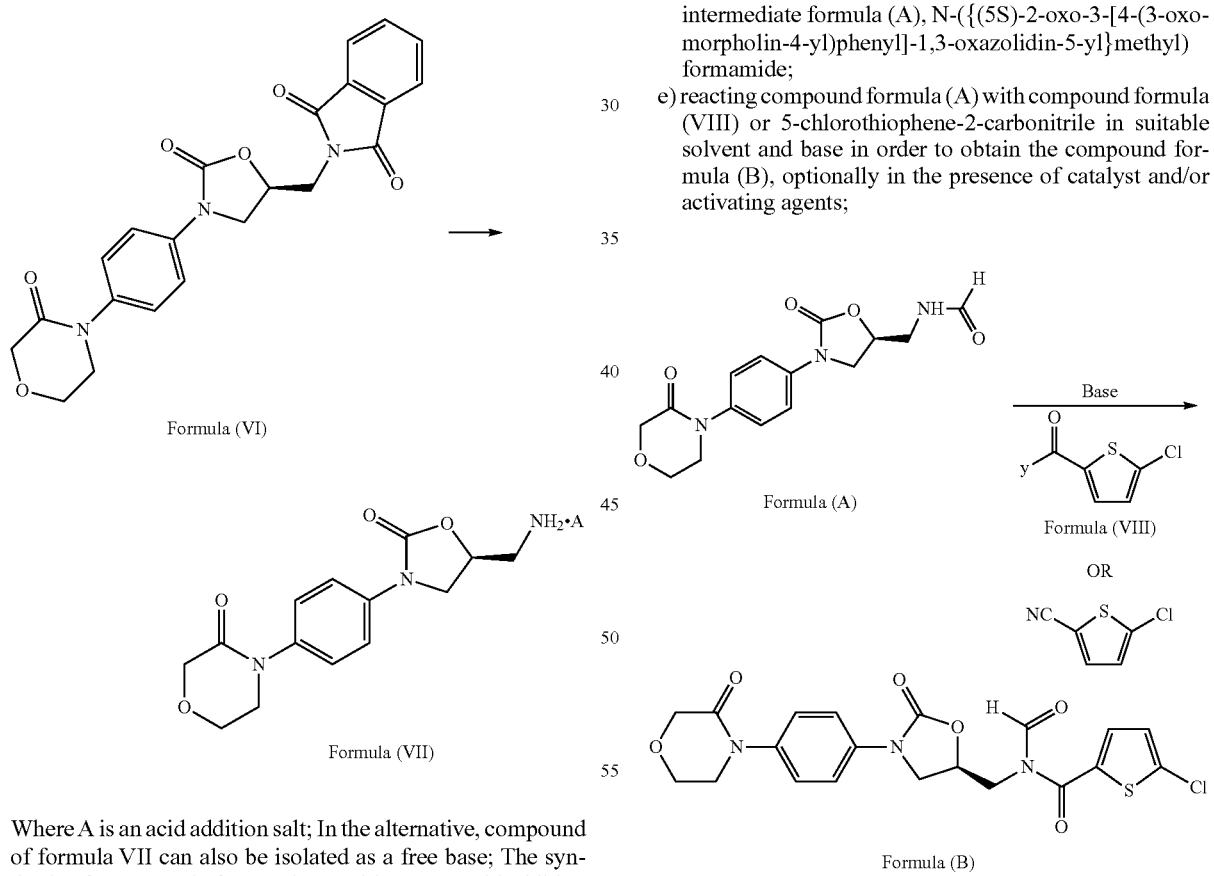

Where A is an acid addition salt; In the alternative, compound of formula VII can also be isolated as a free base; The synthesis of compound of Formula VII either as an acid addition salt or a free base is known and hence not claimed. Compound of Formula VII may be made by any known method.

d) The compound of formula (VII) with acid addition salt is reacted in the presence of a base with an acid to obtain a novel intermediate formula (A), N-({(5S)-2-oxo-3-[4-(3-oxomorpholin-4-yl)phenyl]-1,3-oxazolidin-5-yl}methyl)formamide;

In the alternative where compound of Formula VII is a free base it is directly reacted with an acid to give a novel intermediate formula (A), N-({(5S)-2-oxo-3-[4-(3-oxo-morpholin-4-yl)phenyl]-1,3-oxazolidin-5-yl}methyl) formamide;

e) reacting compound formula (A) with compound formula (VIII) or 5-chlorothiophene-2-carbonitrile in suitable solvent and base in order to obtain the compound formula (B), optionally in the presence of catalyst and/or activating agents;

Wherein;
Y may be sulfonyloxy, imidazole, triazole, tetrazole, alkoxy, substituted alkoxy, tri-halomethoxy, N-hydroxysuccinamide, hydroxy, esters, primary amine, secondary amine p-nitrophenol, N-hydroxythalamide, N-hydroxybenzotriazole, chlorine, fluorine, bromine & iodine. Base used may be inorganic or organic.

Compound of Formula B, is prodrug of compound of Formula I which is popularly known as rivaroxaban having the structure of formula-I.

Formula (I)

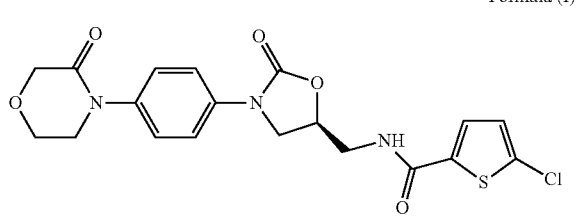

When the aldehyde group of compound of formula B, is eliminated on exposure to an acidic or basic environment, it is converted to the active moiety, Rivaraxoban, Hence Compound formula (B) when treated with acid or base in suitable solvent departs the aldehyde group from compound formula (B), to obtain the title compound Rivaroxaban formula (I);

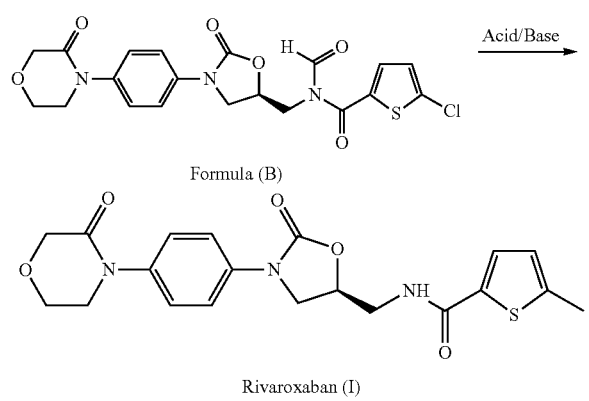 [SMILES: O=CN(C[C@H]1CN(c2ccc(N3CCOCC3=O)cc2)C(=O)O1)C(=O)c1ccc(Cl)s1 ; Cc1ccc(C(=O)NC[C@H]2CN(c3ccc(N4CCOCC4=O)cc3)C(=O)O2)s1]

Formula (B)

Rivaroxaban (I)

The instant invention further extend to the preparation of acid addition salt of compound formula (VII), in order to get the purified compound without any further purification by acid-base treatment, or solvent crystallization.

The solvent used in step (a) and step (c) may be same or different; wherein the said solvent is an organic solvent selected from the group comprising aliphatic hydrocarbons, aromatic hydrocarbons, dialkylformamides, ethers, cyclic ethers, substituted cyclic ethers, alcohol, ketones, dialkylsulfoxides, dialkylacetamides, nitriles, ionic liquids, halogenated aliphatic hydrocarbons and water or mixtures thereof but more preferable solvent which is neutral towards the reactants.

The step (a) could be carried out at temperature in the range of 0° C. to 95° C. Usually the reaction may be carried out at temperature up to reflux temperature of the said solvent.

The solvent used in step (b) for the preparation of compound of formula (VI) is an organic solvent selected from the group comprising of aliphatic hydrocarbons, aromatic hydrocarbons, dialkylformamides, ethers, cyclic ethers, substituted cyclic ethers, ketones, dialkylsulfoxides, dialkylacetamides, nitriles, ionic liquids, halogenated aliphatic hydrocarbons or mixtures thereof.

The solvent used in step (c) is an organic solvent selected from the group comprising aliphatic hydrocarbons, aromatic hydrocarbons, dialkylformamides, ethers, cyclic ethers, substituted cyclic ethers, dialkylsulfoxides, dialkylacetamides, nitriles, ionic liquids, halogenated aliphatic hydrocarbons and water or mixtures thereof. Further the compound formula (VII) may be prepared in terms of acid addition salt by using inorganic or organic acid.

In step (d) the compound of formula (VII) may be used in free base form or its acid addition salt. The solvent used in the step (d) is an organic solvent, may be mixture or water and organic solvent. Formylating agent used in the step (d) may be formic acid, alkyl formate etc. The solvent used in the reaction may be selected for the aromatic hydrocarbons, nitriles, aliphatic hydrocarbons, ethers preferably aromatic hydrocarbon more preferably toluene and xylene. The base used in step (d) is selected from organic or inorganic base.

In step (e) compound formula (A) was treated with formula (VIII) optionally in the presence of base which may be inorganic or organic in solvent selected from the group comprising aliphatic hydrocarbons, aromatic hydrocarbons, dialkylformamides, ethers, cyclic ethers, substituted cyclic ethers, dialkylsulfoxides, dialkylacetamides, nitriles, ionic liquids, esters, halogenated aliphatic hydrocarbons, ketones, cyclic amides and water or mixtures thereof to obtain Rivaroxaban precursor of formula (B). Activating agents used in the reaction of step (e) comprises CDI, DCC, HOBt, DMAP, EDCI, boric acid, boronic acid, phenyl boronic acid etc. and mixture thereof.

According to yet another embodiment, the present invention provides a process for preparation of formula (B);

Formula (B)

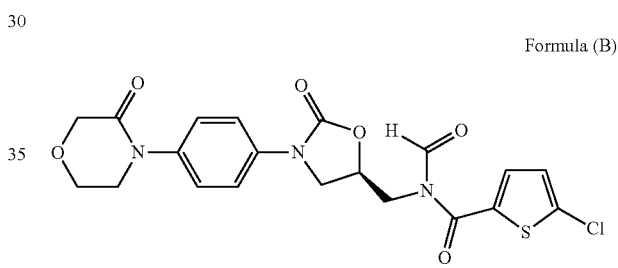

Comprises:
reacting compound formula A)

Formula (A)

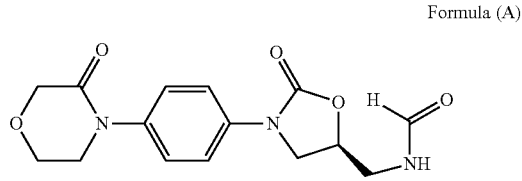 [SMILES: O=CNC[C@H]1CN(c2ccc(N3CCOCC3=O)cc2)C(=O)O1]

with compound of formula (VIII) to obtain compound formula (B)

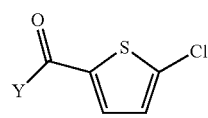

Wherein;
Formula (VIII)
Y may be sulfonyloxy, imidazole, triazole, tetrazole, alkoxy, substituted alkoxy, tri-halomethoxy, N-hydroxysuccinamide, hydroxy, esters, primary amine, secondary amine p-nitrophenol, N-hydroxythalamide, N-hydroxybenzotriazole, chlorine, fluorine, bromine & iodine. Base used may be inorganic or organic.

The solvent used for the said reaction may be inorganic or organic in solvent selected from the group comprising aliphatic hydrocarbons, aromatic hydrocarbons, dialkylformamides, ethers, cyclic ethers, substituted cyclic ethers, dialkylsulfoxides, dialkylacetamides, nitriles, ionic liquids, esters, halogenated aliphatic hydrocarbons, ketones, cyclic amides and water or mixtures thereof to obtain Rivaroxaban precursor of formula (B) Activating agents used in the reaction comprises CDI, DCC, HOBt, DMAP, EDCI, boric acid, boronic acid, phenyl boronic acid etc. and mixture thereof. The base used is selected from organic or inorganic base and optionally compound formula (B) may be purified or can be used as such for next reaction.

According to yet another embodiment of the present invention, recemate of free base or acid addition salt compound of formula (VII) may be done using enzymatic kinetic resolution.

Formula (VII)

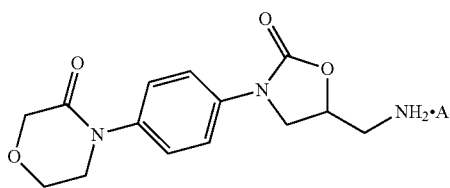

Wherein;
A is acid addition salt; acid may be inorganic or organic acid;

In yet another embodiment of the present invention, the base used in aforementioned step is inorganic or organic and solvent is selected from the group comprising aliphatic hydrocarbons, aromatic hydrocarbons, dialkylformamides, ethers, cyclic ethers, substituted cyclic ethers, dialkylsulfoxides, dialkylacetamides, nitriles, ionic liquids, esters, halogenated aliphatic hydrocarbons, ketones, cyclic amides and water or mixtures thereof to obtain Rivaroxaban of formula (I) Activating agents used in the reaction comprises CDI, DCC, HOBt, DMAP, EDCI, boric acid, boronic acid, phenyl boronic acid etc. and mixture thereof.

As used herein, the term "hydrate" means a compound which further includes a stoichiometric or non-stoichiometric amount of water bound by non-covalent intermolecular forces. As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The present invention is described in the examples given below; further these are provided only to illustrate the invention and therefore should not be construed to limit the scope of the invention.

Example—A

Abbreviations and Acronyms

LC-MS—Coupled Liquid chromatography-mass spectroscopy
HPLC—High performance liquid chromatography
LLQQ—Lower limit of quantification
SD—Standard deviation
AUC—Area under curve
DMSO—dimethyl sulphoxide
NADPH—nicotinamide adenine dinucleotide phosphate-oxida
CYP—cytochrome
BLOQ—below limit of quantification
SIF—Stimulated Intestinal fluid
SGF—Stimulated gastric fluid
CV—Concentration value
C max Highest concentration The following exemplary embodiment in terms of details study illustrates the invention but it is not restricted to these examples with procedure.

Example—1

Preparation of N-({(5S)-2-oxo-3-[4-(3-oxomorpholin-4-yl)phenyl]-1,3-oxazolidin-5-yl}methyl)formamide (Aldehyde of Primary Amine)

In a four neck round bottom flask charged with 4-{4-[(5S)-5-(aminomethyl)-2-oxo-1,3-oxazolidin-3-yl]phenyl}morpholin-3-one free base (50 g) toluene (350 ml) and formic acid (21.63 g). Reaction mass then heated azeotropically to 110-120° C. employing dean-stark apparatus for 3 to 4 h. (water removed azeotropically) Reaction mass is cooled to 25 to 30° C. Obtained solid is filtered off and washed by toluene.

Yield 96%

Example—2

Preparation of 5-chloro-N-formyl-N-({(5S)-2-oxo-3-[4-(3-oxomorpholin-4-yl)phenyl]-1,3-oxazolidin-5-yl}methyl)thiophene-2-carboxamide (Compound Formula-B)

Added N-({(5S)-2-oxo-3-[4-(3-oxomorpholin-4-yl)phenyl]-1,3-oxazolidin-5-yl}methyl)formamide (1 g), dichloromethane (25 ml) in a clean dry 4 neck R.B. flask at 25 to 30° C. To this clear solution added potassium carbonate (0.89 g) and stirred at 25 to 30° C. for 30 minutes. To this reaction mass, slowly added solution of 5-chlorothiophene-2-carbonyl chloride (1.0 g), and dichloromethane (5 ml). The obtained reaction mass then stirred at 25 to 30° C. for 5 to 6 h. Added water (25 ml) to reaction mass and separated organic layer. Obtained organic 4 layer was then washed by water (25 ml×2). Finally organic layer is dried over sodium sulfate and concentrated under reduced pressure to obtain residue. Added methanol (5 ml) to the residue and heated to reflux to get a clear solution. The obtained clear solution was gradually cooled to 15 to 20° C. The precipitated solid then filtered off and washed by chilled methanol (1 ml).

$^1$H-NMR (400 Mz, $d_6$-DMSO), δ=3.74-3.77 (m, 2H), 3.84-3.87 (m, 1H), 4.02-4.05 (m, 2H), 4.07-4.11 (n, 2H), 4.12-4.15 (m, 1H), 4.34-4.41 (m, 3H), 4.94-5.00 (m, 1H), 7.00-7.01 (d, 1H thiophene), 7.30-7.31 (d, 1H thiophene), 7.33-7.37 (dt, 2H aromatic), 7.55-7.58 (dt, 2H aromatic), 9.28 (s, 1H aldehyde)

The example 2 is carried out in different solvents such as acetone, toluene and ether the with the same molar ratio/parts wherein the varies in yield noted below;

| Solvent(s) | yield |
|---|---|
| Acetone | 75% (reaction perform as reflect in example 02) |
| Toluene | 78% (reaction perform as reflect in example 02) |
| Ether | 79% (reaction perform as reflect in example 02) |

Example—3

Preparation of 5-chloro-N-({(5S)-2-oxo-3-[4-(3-oxomorpholin-4-yl)phenyl]-1,3-oxazolidin-5-yl}methyl)thiophene-2-carboxamide (Nitrile Route)

To a solution of 4-{4-[(5S)-5-(aminomethyl)-2-oxo-1,3-oxazolidin-3-yl]phenyl}morpholin-3-one hydrochloride (5.7 g) in ethanol (70 ml) added potassium carbonate (7.1 g) and the mixture was stirred 2 h at 25 to 30° C. then filtered to obtain 4-{4-[(5S)-5-(aminomethyl)-2-oxo-1,3-oxazolidin-3-yl]phenyl}morpholin-3-one (free base). In another flask charged solution of 5-chlorothiophene-2-carbonitrile (2.9 g) under nitrogen in ethanolic HCl (12 ml) and stirred for 5 h at room temperature till white precipitate was obtained. Distilled under nitrogen to avoid from moisture and obtained residue added in solution of 4-{4-[(5S)-5-(aminomethyl)-2-oxo-1,3-oxazolidin-3-yl]phenyl}morpholin-3-one. The mixture was stirred for 16 to 18 h at reflux temperature. Aq. ethanol (5 ml) was and mixture heated at reflux temperature for 10 to 12 h to obtain 5-chloro-N-({(5S)-2-oxo-3-[4-(3-oxomorpholin-4-yl)phenyl]-1,3-oxazolidin-5-yl}methyl)thiophene-2-carboxamide (crud material) which is further purified by column Chromatography.

Example—4

Preparation of N-({(5S)-2-oxo-3-[4-(3-oxomorpholin-4-yl)phenyl]-1,3-oxazolidin-5-yl}methyl)formamide A four neck round bottom flask was charged with 4-{4-[(5S)-5-(aminomethyl)-2-oxo-1,3-oxazolidin-3-yl]phenyl}morpholin-3-one Hydrochloride (250 g), Dichloromethane (1250 ml) and ammonia (250 ml). The solution stirred for 15 min and the layers separated, Added toluene (1250 ml) to the organic layer, along with water (500 ml) and formic acid (140.6 g). Reaction mass was then heated azeotropically to 110-120° C. employing dean-stark apparatus for 3 to 4 h. (water removed azeotropically) Reaction mass was cooled to 25 to 30° C. Obtained solid then filtered off and washed by toluene.
Yield=80.0%

Example—5

Preparation of 5-chloro-N-formyl-N-({(5S)-2-oxo-3-[4-(3-oxomorpholin-4-yl)phenyl]-1,3-oxazolidin-5-yl}methyl)thiophene-2-carboxamide Added N-({(5S)-2-oxo-3-[4-(3-oxomorpholin-4-yl)phenyl]-1,3-oxazolidin-5-yl}methyl)formamide (120 g), dichloromethane (2400 ml) to a clean dry 4 neck R.B. flask at 25 to 30° C. cooled the reaction mass to 0 to 5° C. To this solution added Diisopropylethyl amine (145.7 g) dropwise manner, a solution of 5-chlorothiophene-2-carbonyl chloride (170 g), and dichloromethane (240 ml) at 0 to 5° C. The obtained reaction mass was then stirred at 25 to 30° C. and heated to reflux for 12 hr. The reaction mass was cooled to 25 to 30° C. washed with 10% citric acid solution (2×360 ml), and separated organic layer. Obtained organic layer then washed by water (600 ml×2) and concentrated under reduced pressure to obtain a residue. Added methanol (600 ml) to residue and stirred for 20 min. The precipitated solid was then filtered off, washed by methanol (240 ml), sucked dry and the wet cake taken into a flask methanol (600 ml) added and the solution was then stirred for 30 min., solid then filtered off and washed by methanol (240 ml).
Yield=85.0%

Example—B

Determination of the Stability of the Compound Formula B in SGF and SIF Fluids

The compound formula (B), is dissolved in DMSO and then diluted with methanol:water (90:10. Stability in Buffer at Various pH buffers and SIF/SGF medium are studied:

5.7 mg of the compound formula (B), is weighed into a 2 ml HPLC vial and dissolved in 0.250 ml DMSO. 2 µl of the compound formula (B) solution is added to 250 µl of the respective buffer solution and kept at room temperature on incubator shaker for 24 hr. On completion of incubation period, the solution is centrifuged and supernatant is taken. To the supernatant, ice cold acetonitrile containing IS is added, vortexed and injected into LCMS/MS.

LC/MS/MS Method:

API 4000, ESI Agilent 1100 column: Gemini Nx 100 mm×4.6 mm 5.µ; column temperature: 30° C.; eluent A: 0.1% formic acid in water, eluent B: acetonitrile; gradient: 0-2.5 min 95% A, 5% B; 2.5-2.6 min 5% A, 95% B; 2.6-4.2 min 95% A, 5% B; flow rate: 0.8 ml/min; ESI. Q1:464.098, Q3:144.255

Decomposition of the exemplary compound in these solutions was observed at pH 7.4 and pH 7.8.

(Buffer) Solutions Employed:

Prepared 0.1 mol of citric acid and 0.2 mol of di sodium hydrogen phosphate in water. Buffer pH 2.2, 4 and 7.8 are prepared using citric acid and disodium hydrogen phosphate by adjusting the pH with 0.1N HCl or 1N NaOHpH 7.4: 8.89 g disodium hydrogen phosphate (Solution A) add to 1 liter of water, 1.5601 g sodium di-hydrogen phosphate (solution B) are made up to 1 liter with water; Solution A (19 ml) and Solution B (81 ml) are mixed. SIF/SGF: 2.38 g of SIF original powder (biorelavant media) is dissolved in 1 L of milliQ water. The pH of the solution is adjusted for SIF (7.4) and SGF (2.2) with 0.1N HCl. The ratios of the peak areas (F) at the respective time points in relation to the peak areas at the starting time are calculated In this simulating SIF and SGF study samples, the simulating fluid stability of the compound formula B was evaluated to see the extent the compound remaining in tact at various time points at intestinal and gastric pH condition in comparison against zero minute. The peak area (F) is directly correlated to the amount of test compound which is quantified by the LC MS method.

In simulating intestinal and gastric fluid, the area of the formula B compared with zero minute area to 120 min. The compound area remained the same over 120 min showing stability at intestinal conditions and the similar results were observed at simulating gastric conditions.

In buffer stability at pH 2.2 and 7.4

In this buffer stability of varying pH conditions of pH 2.2, 4 and 7.8, the stability of the compound formula B at various pH conditions was evaluated to see the extent of the compound remaining in tact at specified time points in comparison against zero minute/or single point calibration neat aqueous standard. In these pH conditions of pH 7.4, pH 2.2, there is formation of rivaroxaban which is monitored by LCMS. There is presence of formula B seen which is at pH 2.2 and 4.0 although there is a degradation and conversion to rivaroxaban in these pH conditions.

Interestingly, there is conversion of rivaroxaban which was monitored by LCMS. This proves that the formula B compound is degraded in varying pH buffer conditions and rivaroxaban formation is observed. In buffers of pH there is a conversion to rivaroxaban in in-vitro conditions which is also observed to be translating in the in-vivo conditions supported by evidence in in-vivo rat pharmacokinetic studies in rats. Also there is evidence that conversion to rivaroxaban is found in various in-vitro assays like metabolic stability studies with microsomes and plasma stability studies in mouse, rat and humans.

In this assay, a formation of the rivaroxaban was found, as well as test substance (compound formula B) at various pH conditions. However, the test compound formula B is stable at simulating intestinal conditions. By plotting the comparison of stability of formula B at various pH conditions are well illustrated in Table 1, 2 & 3.

Table 1 represents the stability comparison chart of compound formula B at pH 7.8, pH 4 and pH 2.1.

|  | Sample Name | Analyte Peak Area (counts) | Average | SD | CV |
|---|---|---|---|---|---|
| Compound formula B | pH 2.1 | 20975674<br>35654402 | 28315038 | 162.0453269 | 0.000572294 |
|  | PH 4 | 42841292<br>26917087 | 34879190 | 285.7428233 | 0.000819236 |
|  | pH 7.8 | 35312<br>42503 | 38907.5 | 0.097829461 | 0.000251441 |
|  | Standard | 40131132<br>39542018<br>39876334 | 39849828 | 11.6442782 | 2.92204E−05 |

Table 2 represents the stability comparison chart of compound formula B at simulating intestinal fluid.

| Stability in SIF | Sample Name | Analyte Peak Area (counts) | IS Peak Area (counts) | Area Ratio | Average | SD | CV |
|---|---|---|---|---|---|---|---|
| Compound formula B | Zero min | 38191589<br>39972052 | 165067<br>179662 | 231.371<br>222.485 | 226.928 | 6.2833509 | 2.7688742 |
|  | 30 min | 37765238<br>36339204 | 188499<br>192876 | 200.347<br>188.407 | 194.377 | 8.442855 | 4.3435463 |
|  | 60 min | 35757521<br>36426366 | 194543<br>200580 | 183.803<br>181.606 | 182.7045 | 1.5535136 | 0.8502875 |
|  | 120 min | 34245401<br>33738135 | 200460<br>178638 | 170.834<br>188.863 | 179.8485 | 12.748428 | 7.0884262 |

Table 3 represents the stability comparison chart of compound formula B at simulating gastric fluid.

| Stability in SGF | Sample Name | Analyte Peak Area (counts) | IS Peak Area (counts) | Area Ratio | Average | SD | CV | % Parent remaining | Conclusion |
|---|---|---|---|---|---|---|---|---|---|
| Compound Formula B | Zero min | 34733277<br>32540774 | 186737<br>148905 | 186.001<br>218.533 | 202.267 | 23.003598 | 11.372887 | 100 | Compound Formula B is stable |
|  | 30 min | 32217743<br>36940283 | 147631<br>201482 | 218.232<br>183.343 | 200.7875 | 24.670248 | 12.286745 | 99.27 |  |
|  | 60 min | 35234526<br>35427185 | 174138<br>171198 | 202.336<br>206.937 | 204.6365 | 3.2533983 | 1.5898426 | 101.17 |  |
|  | 120 min | 36170541<br>31588036 | 185892<br>150315 | 194.578<br>210.145 | 202.3615 | 11.007531 | 5.4395383 | 100.05 |  |

2. In Vitro Stability in Rat, Mouse and Human Plasma (LC-MS Detection)

1 mg of the compound formula (B) is weighed into a 1.5 microfuge tube and dissolved in DMSO. The final concentration of the test compound in the assay is 5 micromolar. The compound formula (B) was added to Rat or human plasma or mouse plasma, incubated at 37.degree. C. The 100 microliters of aliquot at time point was removed and and diluted with ice cold acetonitrile containing IS (200.mu·L) to stop the reactions. Samples are centrifuged at 10,000 RPM for 5 minutes to precipitate proteins. Supernatants are transferred to micro centrifuge tubes and stored at −20° C. for analysis of LC/MS/MS. The percent parent remaining of the test substance is calculated as ratio of peak area at each time point to peak area ratio at zero min, multiplied by 100. The compound formula (B) is observed to be converted in to Rivaroxaban.

LC/MS/MS Method:

API 4000, ESI Agilent 1100 column: Gemini Nx 100 mm×4.6 mm 5.1; column temperature: 30° C.; eluent A: 0.1% formic acid in water, eluent B: acetonitrile; gradient: 0-2.5 min 95% A, 5% B; 2.5-2.6 min 5% A, 95% B; 2.6-4.2 min 95% A, 5% B; flow rate: 0.8 ml/min; ESI. Q1:464.098, Q3:144.255

Table-4;

Represent the Plasma stability in Human, Rat and Mouse of the test compound (formula-B) and rivaroxaban three species. Negligible amount of the compound of formula B was observed in in-vitro plasma stability experiment and rapid conversion to rivaroxaban observed in in-vitro conditions using plasma samples from the tested species CYP Inhibition Assay The ability of substances to inhibit CYP1A2, CYP2C9, CYP2D6, CYP2C19, CYP2J2 and CYP3A4 in humans was investigated with pooled human liver microsomes as enzyme source in the presence of standard substrates (see below) which form CYP-isoform-specific metabolites. The inhibitory effects are investigated with eight different concentrations of the test compounds (0.001, 0.01, 0.1, 0.3, 1, 3, 10 μM), compared with the extent of the CYP-isoform-specific metabolite formation of the standard substrates in the absence of the compound formula (B), and the corresponding $IC_{50}$ values are calculated. A standard inhibitor which specifically inhibits a single CYP isoform serves as control of the results obtained.

Procedure:

Incubation of phenacetin, diclofenac, dextromethorphan, mephenotoin, albendazole and testosterone with human liver microsomes in the presence of in each case eight different concentrations of a compound formula (B) (as potential inhibitor) is carried out on an incubator shaker at 37 C. Standard incubation mixtures comprise NADPH and substrates in 100 mM phosphate buffer (pH 7.4) in a total volume of 200 μl.

TABLE 4

Plasma stability in Human, Rat and Mouse of the test compound (formula-B) and rivaroxaban

| | % Parent remaining (Human) | | | % Parent remaining(rat) | | |
|---|---|---|---|---|---|---|
| | Test Product | | | Test Product | | |
| Time(min) | Test Product (Compound formula-B) | Rivaroxaban formation* | Rivaroxaban | Test Product (Compound formula-B) | Rivaroxaban formation | Rivaroxaban |
| 0 | | 100 | 100 | | 100 | 100 |
| 30 | | 95.46 | 100 | | 100 | 82.35 |
| 60 | | 77.84 | 99.68 | | 82.43 | 88.4 |
| Conversion | Conversion to rivaroxaban is seen from zero min. Neglible amount of test product detected | Rivaroxaban formation in Test substance | 99.99%, unchanged, stable in plasma | Conversion to rivaroxaban is seen from zero min. Neglible amount of test product detected | Rivaroxaban formation in Test substance | 88.4%, unchanged, stable in plasma |

| | | % Parent remaining(Mouse) | | |
|---|---|---|---|---|
| | | Test Product | | |
| | Time(min) | Test Product (Compound formula-B) | Rivaroxaban | Rivaroxaban |
| | 0 | | 100 | 100 |
| | 30 | | 100 | 100 |
| | 60 | | 82.18 | 100 |
| | Conversion | Conversion to rivaroxaban is seen from zero min. Neglible amount of test product detected | Rivaroxaban formation in Test substance | unchanged, stable in plasma |

Table 4 shows the stability assay of the compound of formula B, in plasma matrix of rat, mouse and human. The experiment was conducted to determine the stability of the compound of formula B, as well as to see whether the conversion of the formula B compound to rivaroxaban occurs in plasma matrix of mouse, rat and human. Rapid conversion to rivaroxaban was observed in experiments conducted with all Test compound are dissolved in acetonitrile. Incubated with pooled human liver microsomes at 37.degree. C. for a defined time. The reactions are stopped by adding 100 μl of acetonitrile in which a suitable internal standard is always present. Precipitated proteins are removed by centrifugation, and the supernatants analyzed by LC-MS/MS. The data represents the extrapolated $IC_{50}$ (μM) concentration derived from 3 μM.

TABLE 5

CYP inhibition studies IC$_{50}$ (µM) of CYP isoforms

| CYP Isoforms | Test Product(formula B) | Rivaroxaban |
|---|---|---|
| 1A2 | 1.4 | 18.9 |
| 3A4 | 5.7 | 9.7 |
| 2C9 | 22.4 | 16.7 |
| 2C19 | 25.3 | 13.2 |
| 2J2 | 6.7 | No inhibition |
| 2D6 | 8.2 | 13.2 |
| Interpretation | Low drug-drug interaction (compound formula-B with other drug) when administered. | |

| | Permeability in caco2 system | | Efflux |
|---|---|---|---|
| | Papp (10$^{-6}$ cm/sec) | | ratio |
| Compound | A > B | B > A | (B > A/A > B) |
| derivative | 17.41 | 40.3 | 2.31 |
| Interpretation | Derivative showed high permeability. Classification based on Papp. Derivative showed efflux of >2 and observed to be a Pgp substrate. | | |

(10$^{-6}$ cm/sec) <2 = low, 2-20 = medium, >20 = high

Table-5 indicates that the CYP inhibition study using probe substrate method was carried out to determine the concentration required to inhibit different CYP isoforms. This is an essential parameter to gauge drug-drug interactions. The compound of formula B showed minimal inhibition of the CYP isoforms (>1 uM) that were assayed.

3. In Vitro Liver Microsomal Stability Assay

Liver microsomal stability assays are conducted at 1 mg per mL liver microsome protein with an NADPH in phosphate buffer (100 mM, pH 7.4). Test compounds (compound of formula B of the invention) are prepared as solutions in 20% methanol-water and added to the assay mixture (final assay concentration 1 µM) and incubated at 37.degree. C. Aliquots (100.µ·L) are taken out at times 0, 15, and 30 minutes, and diluted with ice cold acetonitrile containing IS (200.mu·L) to stop the reactions. Samples are centrifuged at 10,000 RPM for 5 minutes to precipitate proteins. Supernatants are transferred to micro centrifuge tubes and stored at −20° C. for analysis of LC/MS/MS. The percent parent remaining of the test substance is calculated as Ratio of peak area at each time point to peak area ratio at zero min, multiplied by 100. The compound formula (B) is converted to Rivaroxaban in microsomal assay.

Table-6

Represent Microsomal stability in Human, Rat and Mouse of the test compound (formula-B) and rivaroxaban.

TABLE 6

Microsomal stability in Human, Rat and Mouse of the test compound(formula-B) and rivaroxaban

| | % Parent remaining (Human) | | | % Parent remaining (rat) | | |
|---|---|---|---|---|---|---|
| | Test Product | | | Test Product | | |
| Time(min) | Test Product | Rivaroxaban formation* | Rivaroxaban | Test Product | Rivaroxaban formation | Rivaroxaban |
| 0 | — | 100 | 100 | — | 100 | 100 |
| 15 | — | 100 | 0.01 | — | 19.78 | 0.01 |
| 30 | — | 66.2 | 0.01 | — | 5.20 | 0.02 |
| % metabolised | Metabolised to rivaroxaban, seen from zero min. Neglible amount of test product detected | Rivaroxaban formation in Test substance microsomal protein. Formed rivaroxaban is metatabolied (44.8%) | 99.99% metabolised | Metabolised to rivaroxaban is seen from zero min. Neglible amount of test product detected | Rivaroxaban formation in Test substance in microsomal assay. The formed Rivaroxaban is metabolised (94.8%) | 99.98% metabolised |
| Observation | Formation of rivaroxaban from start of the reaction and formed rivaroxaban is stable in human microsome | | High metabolism | Formation of rivaroxaban from start of the reaction and formed rivaroxaban is shown metabolism | | High metabolism |

| | % Parent remaining(Mouse) | | |
|---|---|---|---|
| | Test Product | | |
| Time(min) | Test Product | Rivaroxaban | Rivaroxaban |
| 0 | — | 100 | 100 |
| 15 | — | 41.93 | 0.03 |
| 30 | — | 25.70 | 0.02 |
| % metabolised | metabolised to rivaroxaban is seen from zero min. Neglible amount of test product detected | Rivaroxaban formation in Test substance in microsomal assay. The formed Rivaroxaban is metabolised (74.3%) | 99.98% Metabolised |

TABLE 6-continued

Microsomal stability in Human, Rat and Mouse of the test compound(formula-B) and rivaroxaban

| | Observation | Formation of rivaroxaban from start of the reaction and formed rivaroxaban is shown metabolism | High metabolism |
|---|---|---|---|

The findings seen in Table 6 suggest that the Test compound formula B is rapidly metabolized across species in rat, mouse and human microsomes. There is immediate conversion to rivaroxaban seen in this microsomal stability experiment by LCMS. The formed Rivaroxaban was also observed to metabolized in the microsomal experiment across species 4. Determination of Plasma Protein Binding A compound solution (1 mM in DMSO) (5 μL), according to the invention is added to the respective plasma matrices of rat or human or mouse (1 ml).

Add 150 ul of phosphate buffer to receiving side of the dialysis well. Add 150 μl of plasma spiked with 5 μM compound formula (B) to the sample side of the dialysis well, dialyse for 6 h. Precipitate with Acetonitrile and dilute samples prior to Table-7

Represent protein binding in Human Rat and Mouse, The plasma protein binding assay of the formula B, was determined in plasma matrix with different species from rat, mouse and human. This is intended to see compound formula B, plasma binding as well as to see whether the conversion of the formula B, compound to rivaroxaban in plasma matrix across species from mouse, rat to human. There was a rapid conversion seen to rivaroxaban in experimental conducted with all three species. Negligible amount of the compound of formula B, was observed in-vitro plasma stability experiment and rapid conversion to rivaroxaban observed at in-vitro conditions across species. The formed rivaroxaban is also bound to plasma protein across species.

TABLE 7

Protein Binding in Human, Rat and Mouse of the test compound (Formula-B) and quantification of rivaroxaban

| | Human Test Product | | Rat Test Product | | Mouse. Test Product | |
|---|---|---|---|---|---|---|
| Time(hr) | Test Product | Rivaroxaban formation | Test Product | Rivaroxaban formation | Test Product | Rivaroxaban |
| Free fraction (%) | NA | 1.34 | NA | 9.39 | NA | 8.41 |
| % Binding | NA | 98.66 | NA | 96.61 | NA | 91.59 |
| Observation | Not quantificable amount of test product. Based on plasma stabilty, there is a conversion to rivaroxaban and formed Rivaroxaban found to be High bound to plasma protein. Formed Rivaroxaban from test product is similar protein binding to rivaroxaban alone. | | Not quantificable amount of test product. Based on plasma stabilty, there is a conversion to rivaroxaban and formed Rivaroxaban found to be moderate-High bound to plasma protein. Formed Rivaroxaban from test product is comparitively low protein binding to Rivaroxaban alone. | | Not quantificable amount of test product. Based on plasma stability, there is a conversion to rivaroxaban and formed Rivaroxaban found to be moderate-High bound to plasma protein. Formed Rivaroxaban from test product is similar protein binding to Rivaroxaban alone. | | analysis in 1.5 ml polypropylene tubes. Remove 50 μl from the sample side of dialysis well and add 50 μl of phosphate buffer +300 μl of acetonitrile containing IS. Remove 50 μl from the buffer side of the dialysis well and add 50 μl of respective matrix plasma +300 μl of ACN. Then vortexed and centrifuged for 5 min, and supernatant is taken and injected into LCMS.

Different test concentration ranging from 0.1 μM to 20 μM are made in methanol:water (90:10). Test solutions are added to the premixed matrix containing plasma:phosphate buffer (50:50). Precipitate with 300 μl of ice cold acetonitrile containing IS, vortexes and centrifuged. Supernatant is taken and injected into LCMS.

Percentage of plasma protein binding was obtained via Equation(2):% Fraction unbound=(concentration on the buffer side/concentration on the sample side)*100

5. Intravenous and Oral Pharmacokinetics in Wistar Rats:

On the day before administration of the substance, a catheter for obtaining blood is implanted in the jugular vein of the experimental animals (male Wistar rats, body weight 200-250 g) under Isofluran® anesthesia.

On the day of the experiment, a defined dose of the compound formula (B) is administered as solution into the tail vein as a bolus administration and oral administration takes place as a suspension or solution. Blood samples (8-12 time points) are taken through the catheter sequentially over the course of 24 h after administration of the substance. The administration volume is 10 ml/kg for oral and 1 ml/kg for IV in male Wistar rats. Intravenous administration is via a formulation of 2% N—N Dimethyl acetamide/ethanol 10%/PEG400 (30%)/water for IV injection (58%) and via Tween80/PEG400/sterile water in the case of oral administration. Removal of blood is after 0.08, 0.25, 0.5, 1, 2, 3, 4, 6, 8 and 12 hours in the case of IV and, blood withdrawn after 0.25, 0.5, 1.0, 2, 3, 4, 6, 8 and 12 hours for oral administration.

Plasma is obtained by centrifuging the samples in heparinized tubes. IS containing Acetonitrile is added to a defined plasma volume per time point to precipitate proteins. After centrifugation, compound formula (B) and, where appropriate, known cleavage products of the compound formula (B) in the supernatant are determined quantitatively using a suitable LC/MS-MS method.

The measured plasma concentrations are used to calculate pharmacokinetic parameters of the test substance and of the active ingredient compound (A) liberated there from, such as AUC, C.sub.max, T.sub.½ (half-life) and CL (clearance).

After i.v. administration of the compounds, the test substance was no longer detectable in plasma even at the first measurement point. Only the active ingredient was detectable up to the 24-hour time point too.

After oral administration of the compounds, these substances were no longer detectable in plasma even at the first measurement point. Only the active ingredient (Example 1) was detectable up to the 24-hour time point too.

Acetonitrile containing IS is added to the study samples, calibration samples and QCs, and the protein is precipitated using acetonitrile. Vortexed and centrifuged at 4000 rpm and the supernatant is injected by LC-MS/MS (API 4000, AB Sciex). Chromatographic separation is carried out on an Shimadzu UFLC. The injection volume is 10 µl. The separation column used is a Phenomenex Gemini NX 4.6×5µ. 100 mm, adjusted to a temperature of 30.degree. C. A binary mobile phase gradient at 800.mu·l/min is used (A: 0.1% formic acid in water, B: acetonitrile: API 4000, ESI Agilent 1100 column: Gemini Nx 100 mm×4.6 mm 5.µ; column temperature: 30° C.; eluent A: 0.1% formic acid in water, eluent B: acetonitrile; gradient: 0-2.5 min 95% A, 5% B; 2.5-2.6 min 5% A, 95% B; 2.6-4.2 min 95% A, 5% B; flow rate: 0.8 ml/min; ESI. Q1:464.098, Q3:144.255 The temperature of the Turbo V ion source is 500.degree. C. The following MS instrument parameters are used: curtain gas 20 units, ion spray voltage 5 kV, gas 1 50 units gas 2 50 units, CAD gas 6 units. The substances are quantified by peak heights or areas using extracted ion chromatograms of specific MRM experiments.

The plasma concentration/time plots determined are used to calculate the pharmacokinetic parameters such as AUC, C.sub.max, MRT (mean residence time), t.sub.½ (half life) and CL (clearance) employing the validated pharmacokinetic calculation programs.

6. Suspension for Intravenous Administration:
Composition:
2.2 mg of the compound according to the invention, 0.22 of ethanol (10%), 0.66 ml of PEG400 (30%), 1.27 ml of water for injection (58%) and 0.04 ml of 2% N—N-dimethyl acetamide.

A single dose of 1 mg of the compound according to the invention corresponds to 1 ml of intravenous solution.

Preparation:
The required quantity of the test compound is weighed in glass vial. To this, N, N dimethyl acetamide was added and vortexed. Then ethanol, PEG400 was added and vortexed. Finally, water for injection is added, mixed, vortexed and sonicated to achieve the final concentration of 1 mg/ml. The final solution was clear and colorless in appearance.

7. Solution for Oral Administration:
Composition:
8.3 of the compound formula (B), Tween 80, PEG400 and sterile water for injection was added. The required quantity of the test compound is weighed in glass vial. To this, N, N dimethyl acetamide was added and vortexed. Then ethanol, PEG400 was added and vortexed. Finally, water for injection is added, mixed, vortexed and sonicated to achieve the final concentration of 1 mg/ml. The final solution was clear and colorless in appearance Preparation:
The required quantity of the compound formula (B) is weighed in glass vial. To this, Tween 80 was added and vortexed. Then ethanol, PEG400 was added and vortexed. Finally, water for injection is added, mixed, vortexed and sonicated to achieve the final concentration of 0.5 mg/ml. The final solution was clear and colorless in appearance.

Concentration-time profile of Rivaroxaban following intravenous administration of test compound at a dose of 10 mg/kg.

TABLE 8

| PK parameter | Unit | Rivaroxaban alone Mean IV (1 mg/kg) | Mean PO (10 mg/kg) |
|---|---|---|---|
| F | [%] | n.c. | 81.99 |
| AUC(0-t) | [ng/mL*h] | 1002.09 | 8481.44 |
| AUC | [ng/mL*h] | 1102.73 | 9040.96 |
| Δ AUC | [%] | 7.11 | 6.01 |
| C0(tdose) | [ng/mL] | 581.14 | n.c. |
| C(max) | [ng/mL] | n.c. | 1420.27 |
| t(max) | [h] | n.c. | 1.42 |
| t(½, z) | [h] | 6.08 | 5.70 |
| MRT | [h] | 3.38 | 6.29 |
| CL | [mL/min/kg] | 25.33 | 18.75 |
| V(z) | [L/kg] | 10.72 | 9.13 |

Concentration-time profile of Rivaroxaban following oral administration of test compound at a dose of 10 m/kg

TABLE 9

| PK parameter | Unit | Derivative (Rivaroxaban formed on dosing of derivative) Mean IV (1 mg/kg) | Mean PO (10 mg/kg) |
|---|---|---|---|
| F | [%] | n.c. | 26.95 |
| AUC(0-t) | [ng/mL*h] | 3859.31 | 10398.42 |
| AUC | [ng/mL*h] | 3906.91 | 10530.40 |
| Δ AUC | [%] | 1.51 | 1.49 |
| C0(tdose) | [ng/mL] | 559.12 | n.c. |
| C(max) | [ng/mL] | n.c. | 2022.31 |
| t(max) | [h] | n.c. | 1.67 |
| t(½, z) | [h] | 6.61 | 3.69 |
| MRT | [H] | 2.50 | 4.97 |
| CL | [mL/min/kg] | 4.47 | 17.63 |
| V(z) | [L/kg] | 2.78 | 5.84 |

Table 8 and 9 indicate that compound formula B showed an increased exposure in terms of AUC as well as increased C max as compared to Rivaroxaban. This suggests that compound formula B is quickly absorbed and immediately converted to Rivaroxaban.

8. Determination of Anticoagulant Activity

The anticoagulant action of the test substance (compound formula-B) and rivaroxaban was determined in vitro using human plasma. The human plasma used for this experiment was separated from the blood collected in sodium citrate as anticoagulant. The prothrombin time (PT) was determined by using a commercial test kit (Neoplastin from Stagid) and APTT was determined using (Synthasil kit by IL). Different concentrations of test substance and rivaroxaban used were from 0.1 to 1.0 µg/mL along with corresponding solvent as control. For determination of PT the test compound and Rivaroxaban were incubated with the plasma at 37° C. for 10 minutes. Coagulation was then started by addition of thromboplastin, and time when coagulation occurred was determined. The concentration of test substance which effected a doubling of prothrombin time was determined. For determination of a PTT the test compound and Rivaroxaban were incubated with the plasma at 37° C. for 10 minutes after which CaCl2 was added. The results of assay indicated that the test compound (compound formula-B) has significant anticoagulant activity.

In an embodiment of this invention, the compound of formula B can be comprised in medicament normally together with one or more inert, non-toxic, pharmaceutically suitable excipients and to the use thereof for the aforementioned purposes.

The compounds can be administered to act systemically and/or locally. For this purpose, they can be administered in a suitable way and form such as, for example, by the oral, parenteral, pulmonary or nasal route, preferably orally.

Suitable for oral administration are administration forms which function according to the prior art and deliver the compound according to the invention rapidly and/or in modified fashion, and which contain the compounds according to the invention in crystalline and/or amorphous and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

9. Intravenous and Oral Excretion Profile in Wistar Rats:

On the day before administration of the substance, a catheter for obtaining blood is implanted in the jugular vein of the experimental animals (male Wistar rats, body weight 200-250 g) under Isoflurane. anesthesia.

On the day of the experiment, a defined dose of the compound formula (B) is administered as solution into the tail vein as a bolus administration and oral administration takes place as a suspension or solution. Urine and faeces are taken collected from metabolic cages over the course of 144 h after administration of the substance. The administration volume is 10 ml/kg for oral and 1 ml/kg for IV in male Wistar rats. Intravenous administration is via a formulation of 2% N—N Dimethyl acetamide/ethanol 10%/PEG400 (30%)/water for IV injection (58%) and via Tween80/PEG400/sterile water in the case of oral administration. Urine and faeces collection is 0-4, 4-8, 8-24, 24-48, 48-72, 72-96, 96-120, 120-144 in the case of IV and for oral administration.

Urine and faeces was processed and IS containing Acetonitrile is added to a defined urine/faeces and precipitated. After centrifugation, compound formula (B) and, where appropriate, known cleavage products of the compound formula (B) in the supernatant are determined quantitatively using a suitable LC/MS-MS method.

The measured urine and faeces concentrations are used to calculate parameters of the test substance and of the active ingredient compound (A) liberated there from, such as AUC and $C_{max}$.

After i.v. administration of the compounds, the test substance was no longer detectable in urine and faeces even at the first measurement point. Only the active ingredient was detectable up to in both urine and faeces.

After oral administration of the compounds, these substances were no longer detectable in urine and faeces even at the first measurement point. Only the active ingredient (Example 1) was detectable in urine as well as in faeces.

Acetonitrile containing IS is added to the study samples, calibration samples and QCs, and the protein is precipitated using acetonitrile. Vortexed and centrifuged and the supernatant is injected by LC-MS/MS (API 4000, AB Sciex). Chromatographic separation is carried out on an Shimadzu UFLC. The injection volume is 10 µl. The separation column used is a Phenomenex Gemini NX 4.6×5µ. 100 mm, adjusted to a temperature of 30.degree. C. A binary mobile phase gradient at 800.mu·l/min is used (A: 0.1% formic acid in water, B: acetonitrile: API 4000, ESI Agilent 1100 column: Gemini Nx 100 mm×4.6 mm 5.µ; column temperature: 30° C.; eluent A: 0.1% formic acid in water, eluent B: acetonitrile; gradient: 0-2.5 min 95% A, 5% B; 2.5-2.6 min 5% A, 95% B; 2.6-4.2 min 95% A, 5% B; flow rate: 0.8 ml/min; ESI. Q1:464.098, Q3:144.255 The temperature of the Turbo V ion source is 500.degree. C. The following MS instrument parameters are used: curtain gas 20 units, ion spray voltage 5 kV, gas 1 50 units gas 2 50 units, CAD gas 6 units. The substances are quantified by peak heights or areas using extracted ion chromatograms of specific MRM experiments.

10. Suspension for Intravenous Administration:
Composition:
2.2 mg of the compound according to the invention, 0.22 of ethanol (10%), 0.66 ml of PEG400 (30%), 1.27 ml of water for injection (58%) and 0.04 ml of 2% N—N-dimethyl acetamide.

A single dose of 1 mg of the compound according to the invention corresponds to 1 ml of intravenous solution.

Preparation:
The required quantity of the test compound is weighed in glass vial. To this, N, N dimethyl acetamide was added and vortexed. Then ethanol, PEG400 was added and vortexed. Finally, water for injection is added, mixed, vortexed and sonicated to achieve the final concentration of 1 mg/ml. The final solution was clear and colorless in appearance.

11. Solution for Oral Administration:
Composition:
compound formula (B), Tween 80, PEG400 and sterile water for injection was added. The required quantity of the test compound is weighed in glass vial. To this, N, N dimethyl acetamide was added and vortexed. Then ethanol, PEG400 was added and vortexed. Finally, water for injection is added, mixed, vortexed and sonicated to achieve the final concentration of 1 mg/ml. The final solution was clear and colorless in appearance Preparation:
The required quantity of the compound formula (B) is weighed in glass vial. To this, Tween 80 was added and vortexed. Then ethanol, PEG400 was added and vortexed. Finally, water for injection is added, mixed, vortexed and sonicated. The final solution was clear and colorless in appearance.

Concentration-time profile of Rivaroxaban following intravenous administration of test compound (compound formula B) at a dose of 1 mg/kg and oral administration of test compound at a dose of 10 mg/kg

TABLE 10 (A)

| Group | Animal weights (g) | Dose (mg/kg) | Dose volume (mL/kg) | Dose conc. (mg/mL) | Dosing route | Number of animals | Sample time (h) for urine/faeces |
|---|---|---|---|---|---|---|---|
| 1 | 250-300 | 1 | 1 | 1 | i.v. | 3 | 0-4, 4-8, 8-24, 24-48, 48-72, 72-96, 96-120, 120-144 |
| 2 | 250-300 | 10 | 10 | 1 | p.o. | 3 | 0-4, 4-8, 8-24, 24-48, 48-72, 72-96, 96-120, 120-144 |

TABLE 10 (B)

| | Rivaroxaban (IV 1 mg/Kg) | | Rivaroxaban (PO 10 mg/Kg) | | Derivative (IV 1 mg/Kg) | | Derivative (PO 10 mg/Kg) | |
|---|---|---|---|---|---|---|---|---|
| Time [h] | Mean (ng) Urine | Mean (ng/G) Faeces | Mean (ng) Urine | Mean (ng/G) Faeces | Mean (ng) Urine | Mean (ng/G) Faeces | Mean (ng) Urine | Mean (ng/G) Faeces |
| 4 | 559.4 | 442.8 | 2381.3 | 5458.8 | 345.5 | 3122.7 | 1200.6 | 9675.3 |
| 8 | 28.9 | 1442.0 | 1770.9 | 19583.2 | 447.0 | 911.6 | 1828.5 | 11184.7 |
| 24 | 169.4 | 1328.8 | 1838.1 | 236961.7 | 451.5 | 614.6 | 3296.0 | 6274.2 |
| 48 | 333.6 | 342.8 | 464.5 | 35049.4 | 24.6 | 164.5 | 1166.5 | 4881.3 |
| 72 | 539.5 | 110.7 | 236.1 | 6655.8 | 20.0 | 7.4 | 130.8 | 360.4 |
| 96 | 41.9 | 32.6 | 22.9 | 2291.2 | 7.1 | 3.3 | 92.5 | 5.0 |
| 120 | BLQ | 40.3 | 48.4 | 63.9 | BLQ | 5.2 | 30.6 | 45.0 |
| 144 | BLQ | 16.8 | 30.4 | 57.4 | 4.2 | BLQ | 29.7 | 70.7 |

TABLE 10 (C)

| Summary Results | | | | |
|---|---|---|---|---|
| | oral(10 mg/kg) | | IV(1 mg/kg) | |
| | rivaroxaban | derivative | rivaroxaban | derivative |
| urine(ng) | 6720.4 | 7744.6 | 1425.9 | 1152.8 |
| faeces(ng/g) | 408546.9 | 32503.0 | 2937.9 | 4974.9 |
| plasma-AUC | 9041.0 | 10530.4 | 1102.7 | 3906.9 |
| Mean Urine AUC | 76389.7 | 121079.3 | 20998.3 | 55548.0 |
| Mean Faeces AUC | 8189000.0 | 354379.0 | 12537.0 | 30631.7 |
| Tmax | 1.4 | 1.7 | 581.2 | 559.1 |

Table 10 (A), 10 (B) and 10 (C), indicate that, Plasma exposure is higher in Test product (compound formula-B) than the Rivaroxaban. The Urine excretion profile of Rivaroxaban and test compound (compound formula-B) showed similar excretion profile but the unabsorbed rivaroxaban is lesser on oral administration of Test product (compound formula-B).

Compound formula (B), showed lesser amount of rivaroxaban present in faeces as compared to rivaroxaban alone. Which indicate that an advantageous in having higher exposure in plasma and lower excretion in faeces as compared to rivaroxaban.

We claim:
1. A compound of formula (B):

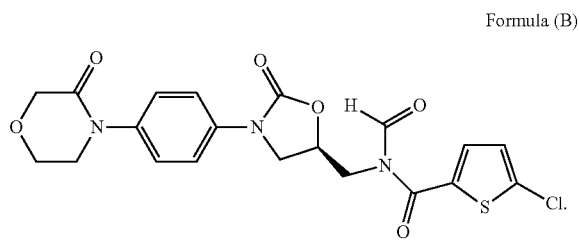 [SMILES: O=CN(C[C@H]1CN(c2ccc(N3CCOCC3=O)cc2)C(=O)O1)C(=O)c1ccc(Cl)s1]

Formula (B)

2. A method for preparation of the compound of formula (B) as claimed in claim 1, comprising:
   a) treating the compound of formula (VII), with an organic acid in suitable solvent(s) to obtain an intermediate of formula (A), N-({(5S)-2-oxo-3-[4-(3-oxomorpholin-4-yl)phenyl]-1,3-oxazolidin-5-yl}methyl)formamide; and

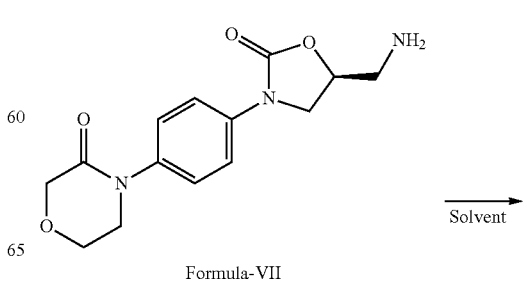

Formula-VII

-continued

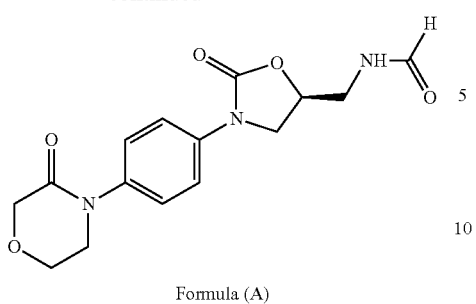

Formula (A)

b) treating the compound of formula (A), with a compound of formula (VIII) or 5-chlorothiophene-2-carbonitrile, in suitable solvents selected from methylene dichloride, acetone, toluene and ether or mixtures thereof in the presence of a base to obtain the compound of formula (B),

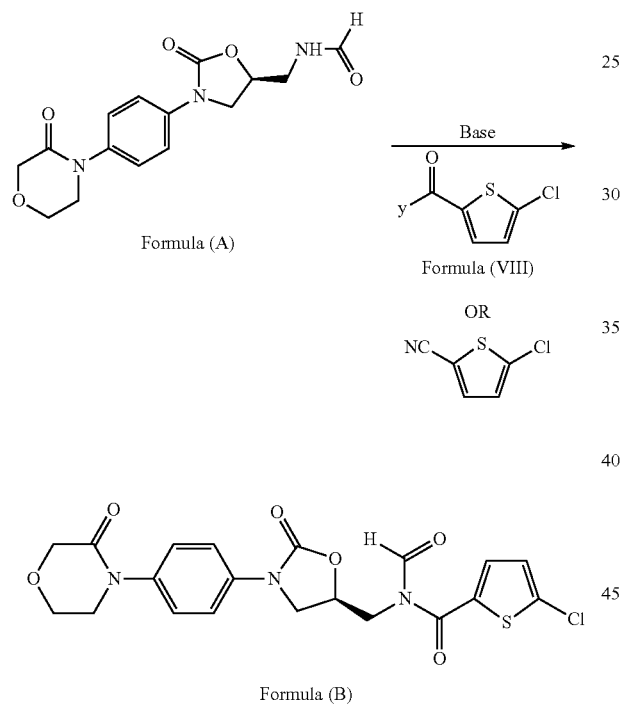

Formula (A)

Formula (VIII)

OR

Formula (B)

wherein Y is sulfonyloxy, imidazole, triazole, tetrazole, alkoxy, substituted alkoxy, tri-halomethoxy, N-hydroxysuccinamide, hydroxy, esters, primary amine, secondary amine p-nitrophenol, N-hydroxythalamide, N-hydroxybenzotriazole, chlorine, fluorine, bromine or iodine.

3. A method for preparation of the compound of formula (B) as claimed in claim 1, comprising:

a) treating an acid addition salt of the compound of formula (VII) with a base in suitable solvent(s) to obtain a base of the compound of formula (VII), which is further treated with an organic acid in suitable solvent(s) to obtain an intermediate formula (A), N-({(5S)-2-oxo-3-[4-(3-oxo-morpholin-4-yl)phenyl]-1,3-oxazolidin-5-yl}methyl)formamide; and Formula-VII $\xrightarrow{\text{Solvent}}$ Formula (A)

A=acid addition salt;

b) treating the compound of formula (A), with a compound of formula (VIII) or 5-chlorothiophene-2-carbonitrile in suitable solvents selected from methylene dichloride, acetone, toluene and ether or mixture thereof in the presence of the base to obtain the compound of formula (B), Formula (A)

$\xrightarrow{\text{Base}}$

Formula (VIII)

OR

Formula (B)

wherein Y is sulfonyloxy, imidazole, triazole, tetrazole, alkoxy, substituted alkoxy, tri-halomethoxy, N-hydroxysuccinamide, hydroxy, esters, primary amine, secondary amine p-nitrophenol, N-hydroxythalamide, N-hydroxybenzotriazole, chlorine, fluorine, bromine or iodine.

4. The method as claimed in claim 2, wherein the organic acid is one or more carboxylic acids selected from the group consisting of formic acid, oxalic acid, and succinic acid.

5. The method as claimed in claim 2, wherein the compound of formula (B) is purified by a combination of one or more of the process of washing, sedimentation, filtration, drying and/or distillation.

6. A pharmaceutical composition comprising the compound of formula (B), as claimed in claim 1, with a combination of suitable pharmaceutically acceptable excipients.

7. An anti-coagulant comprising the compound of formula (B) as claimed in claim 1.

8. The method as claimed in claim 3, wherein the organic acid is one or more carboxylic acids selected from the group consisting of formic acid, oxalic acid, and succinic acid.

9. The method as claimed in claim 3, wherein the compound of formula (B) is purified by a combination of one or more of the process of washing, sedimentation, filtration, drying and/or distillation.

* * * * *